United States Patent
Andersen et al.

(10) Patent No.: US 12,138,310 B2
(45) Date of Patent: Nov. 12, 2024

(54) PROCESSING METHOD FOR BIOPOLYMERS USING SOLVENT COMBINATIONS

(71) Applicant: SolyPlus GmbH, Haselund (DE)

(72) Inventors: Richard Dolph Andersen, Berlin (DE); Annette Assogba-Zandt, Berlin (DE); Elena Maltseva, Schöneiche (DE); Andreas Voigt, Berlin (DE)

(73) Assignee: SolyPlus GmbH, Haselund (DE)

( * ) Notice: Subject to any disclaimer, the term of this patent is extended or adjusted under 35 U.S.C. 154(b) by 91 days.

(21) Appl. No.: 16/753,482

(22) PCT Filed: Oct. 9, 2018

(86) PCT No.: PCT/IB2018/057790
§ 371 (c)(1),
(2) Date: Apr. 3, 2020

(87) PCT Pub. No.: WO2019/073363
PCT Pub. Date: Apr. 18, 2019

(65) Prior Publication Data
US 2020/0254102 A1  Aug. 13, 2020

(30) Foreign Application Priority Data
Oct. 12, 2017 (DE) .......................... 102017009801.8

(51) Int. Cl.
*A61K 47/36* (2006.01)
*A61K 9/14* (2006.01)

(52) U.S. Cl.
CPC .............. *A61K 47/36* (2013.01); *A61K 9/146* (2013.01)

(58) Field of Classification Search
CPC ................................ A61K 47/36; A61K 9/146
See application file for complete search history.

(56) References Cited

U.S. PATENT DOCUMENTS

2013/0136774 A1  5/2013  Voigt et al.

FOREIGN PATENT DOCUMENTS

| GB | 2218429 A | * 11/1989 | ............. A61K 8/735 |
|---|---|---|---|
| JP | 2015-502354 A | 1/2015 | |
| WO | 2008100044 A1 | 8/2008 | |

OTHER PUBLICATIONS

Foglarova et al (Year: 2016).*
Mitsuo et al, machine Translation (Year: 2009).*
Park et al,SciFinder Scholar Abstract Translation (Year: 2015).*
Wang et al (Year: 2016).*
Sugitani, Machine Translation & SciFinder Scholar Abstract Translation (Year: 1990).*
Mitsuo, Machine Translation (Year: 2009).*
Park, SciFinder Scholar Abstract Translation (Year: 2015).*
CN1760214A, Machine Translation (Year: 2006).*
JP2008179710A, Machine Translation (Year: 2008).*
Wang (Year: 2016).*
Park (Year: 2015).*
Hadley et al (Year: 2013).*
Office Action issued on Jun. 23, 2022 in corresponding Japanese Application No. 2020-542213; 5 pages including English-language translation.
Preliminary Office Action 6.23 and Brazillian Search Report published on Aug. 16, 2022 in connection with corresponding Brazilian Application No. 112020006808-0; 9 pages including English-language translation.
Decision of Refusal issued on Dec. 7, 2022, in corresponding Japanese Application No. 2020-542213, 4 pages.
Extended European Search Report issued on Nov. 29, 2023, in corresponding European Application No. 23176851.6, 8 pages.

* cited by examiner

*Primary Examiner* — Jeffrey S Lundgren
*Assistant Examiner* — Ibrahim D Bori
(74) *Attorney, Agent, or Firm* — Maier & Maier, PLLC

(57) ABSTRACT

The invention relates primarily to a processing method of biopolymers by means of solvent/solvent mixtures or multiphase solvent systems by means of which said polymers can be changed in their mechanical and qualitative features and processed more easily.

11 Claims, 2 Drawing Sheets providing a biopolymer in dry particulate form optionally providing at least one active pharmaceutical ingredient providing a single-phase multicomponent system of solvents homogenizing the mixture by mechanical means providing a biopolymer in dry particulate form optionally providing at least one active pharmaceutical ingredient providing a multiphase system of solvents homogenizing the given ingredients by mechanical energy input until a homogeneous mixture is obtained

PROCESSING METHOD FOR BIOPOLYMERS USING SOLVENT COMBINATIONS

PRIORITY CLAIM

This PCT International Patent Application herein claims priority to German priority patent application serial number 102017009801.8, filed Oct. 12, 2017, the entire contents of which are incorporated herein in its entirety.

FIELD OF THE INVENTION

The invention relates primarily to a processing method of biopolymers by means of solvent/solvent mixtures or multiphase solvent systems by means of which said polymers can be changed in their mechanical and qualitative features and processed more easily.

BACKGROUND

Pharmaceutical formulations or medicaments typically consist of one or more active substances which are converted into a suitable galenic form by means of excipients. Active ingredients may have a pharmacological, immunological or metabolic active effect on a human or animal subject and are useful for the prevention, treatment or cure of one or more diseases. Active ingredients may have natural origin, can be synthetically produced or by biotechnological recombinant methods.

In order to make said active ingredients applicable in an efficient and plausible manner, good galenics are necessary, which depend on the type, quantity and intended effect of the active substance. Examples of known drug formulations are solid (tablets, powders, suppositories, hard capsules, soft capsules, micro needles, etc.), semi-solid (creams, ointments, emulsions, gels, suspensions, etc.) and liquid (solutions, foams, etc.)

and can be applied in various ways (for example, peroral, buccal, intravascular, intramuscular, intraocular, subcutaneous, topical, vaginal, rectal, nasal, etc.). Due to these numerous dosage forms, the large spectrum of active ingredients and the need to apply an active ingredient over a sufficient period of time with the right dosage and a good bioavailability, there is a high demand for new developments in the field of galenics and drug delivery. Especially for the application of biotherapeutics, novel formulations are needed that do not destroy the drug in their processing.

Due to the numerous and diverse advantages of (bio-) polymers (including, but not limited to, high biocompatibility, good biodegradability, low negative impact on the environment, production by extraction out of natural resources, low reactivity towards active agents and many more polymer-type dependent advantages) there is a high need in the cosmetic and pharmaceutical field for a lot of different products. However, depending on the type, amount and intended use of said biopolymers, processing problems and quality issues typically must be solved. These issues include, for example, sterility, reproducible quality in production, stability, purity and avoidance of degradation products, etc.

In view of the above, there is a significant, long-felt and yet unmet need for improved processing methods for utilizing biopolymers.

SUMMARY OF REPRESENTATIVE EMBODIMENTS OF THE INVENTION

It is to be understood that the present invention contemplates certain representative methods and formulations, such as for example certain methods and formulations described herein, in which at least one active pharmaceutical ingredient is present.

It is also to be understood that the present invention also contemplates other representative methods, processes and formulations in which no active pharmaceutical ingredients are present or used at any point during the methods or processes, and therefore the present invention also contemplates formulations in which no active pharmaceutical ingredients are present in the final formulations. Therefore, when certain representative methods, processes and formulations are described herein, it is also to be understood that the present invention also contemplates that such methods, processes and formulations can be adapted or modified in an appropriate and suitable manner, as needed or desired, such that no active pharmaceutical ingredients are present or used at any point during the methods or processes, such that no active pharmaceutical ingredients are present in the final formulations.

Therefore it is to be understood that the methods and processes of the present invention, of which several examples are described herein, can be practiced and implemented in such a manner such that including at least one active pharmaceutical ingredient is optional.

According to one embodiment of the present invention, a method of processing a biopolymer comprises: providing a biopolymer in dry particulate form; optionally providing at least one active pharmaceutical ingredient; providing a single-phase multicomponent system of solvents; and homogenizing the mixture by mechanical means. According to another embodiment, the method further comprises removal of excess solvent. According to yet another embodiment, the biopolymer is hyaluronic acid.

According to another embodiment of the present invention, a method of processing a biopolymer comprises: providing a biopolymer in dry particulate form; optionally providing at least one active pharmaceutical ingredient; providing a multiphase system of solvents; and homogenizing the given ingredients by mechanical energy input until a homogeneous mixture is obtained. According to another embodiment, the method further comprises removal of excess solvent. According to yet another embodiment, the biopolymer is hyaluronic acid.

While certain embodiments utilize at least one active pharmaceutical ingredient in dry particulate form, it is also to be understood that the present invention also contemplates that the methods, processes and formulations of the present invention may, in other embodiments, also utilize one or more active pharmaceutical ingredients that are present in any other type of physical state, as well as active pharmaceutical ingredients dissolved in any suitable and appropriate solvent system as needed or desired.

DESCRIPTION OF PREFERRED EMBODIMENTS OF THE INVENTION

Figure 1:
FIG. 1 depicts one representative method of processing a biopolymer.
Figure 1:
Figure 1:
Figure 2:
FIG. 2 depicts another representative method of processing a biopolymer.
Figure 2:
Figure 2:

Reference will now be made in detail to various aspects of the invention and embodiments. The following language and descriptions of certain preferred embodiments of the present invention are provided to further an understanding of the principles of the present invention. However, it will be understood that no limitations of the present invention are intended, and that further alterations, modifications, and applications of the principles of the present invention are also included. For example, the information (including, but not limited to, quantity of ingredients, equipment parameters, reaction conditions, etc.) described herein for the manufacturing examples are only for purposes of illustrating the full scope of the invention.

Terms such as fabrication, manufacturing, processing or producing may be used interchangeably herein.

In accordance with the present invention, polymer-based raw materials can be produced from which many possible products can be derived by further processing, for example for the application of active substances, for efficient administration of cosmetically active substances, for implantation into the body, for wound dressing, etc.

It is to be understood that the present invention contemplates certain representative methods and formulations, such as for example certain methods and formulations described herein, in which at least one active pharmaceutical ingredient is present.

It is also to be understood that the present invention also contemplates other representative methods, processes and formulations in which no active pharmaceutical ingredients are present or used at any point during the methods or processes, and therefore the present invention also contemplates formulations in which no active pharmaceutical ingredients are present in the final formulations. Therefore, when certain representative methods, processes and formulations are described herein, it is also to be understood that the present invention also contemplates that such methods, processes and formulations can be adapted or modified in an appropriate and suitable manner, as needed or desired, such that no active pharmaceutical ingredients are present or used at any point during the methods or processes, such that no active pharmaceutical ingredients are present in the final formulations.

Therefore it is to be understood that the methods and processes of the present invention, of which several examples are described herein, can be practiced and implemented in such a manner such that including at least one active pharmaceutical ingredient is optional.

According to one embodiment of the present invention, a method of processing a biopolymer comprises: providing a biopolymer in dry particulate form; optionally providing at least one active pharmaceutical ingredient in dry particulate form; providing a single-phase multicomponent system of solvents; and homogenizing the mixture by mechanical means. According to another embodiment, the method further comprises removal of excess solvent. According to yet another embodiment, the biopolymer is hyaluronic acid.

According to another embodiment of the present invention, a method of processing a biopolymer comprises: providing a biopolymer in dry particulate form; optionally providing at least one active pharmaceutical ingredient in dry particulate form; providing a multiphase system of solvents; and homogenizing the given ingredients by mechanical energy input until a homogeneous mixture is obtained. According to another embodiment, the method further comprises removal of excess solvent. According to yet another embodiment, the biopolymer is hyaluronic acid.

While certain embodiments utilize at least one active pharmaceutical ingredient in dry particulate form, it is also to be understood that the present invention also contemplates that the methods and processes of the invention may, in other embodiments, also utilize one or more active pharmaceutical ingredients that are present in any other type of physical state, as well as active pharmaceutical ingredients dissolved in any suitable and appropriate solvent system as needed or desired.

In accordance with the present invention, it is to be understood that a polymer or biopolymer (or in the plural, polymers or biopolymers) can include, but are not limited to, one or more of the following substances or classes of substances: proteins, polysaccharides, hydrocarbons, nucleic acids, aptamers, collagen, collagen-n-hydroxysuccinimide, fibrin, gelatin, albumin, alginates, blood plasma proteins, milk proteins, casein, protein-based polymers, hyaluronic acid, chitosan, pectins, gummi arabicum and other gums, casein, whey proteins, gluten, starch, cellulose, synthetic polymers for pharmaceutical or cosmetic applications, like polylactic acid, polyglycolic acid, cell lysates of plants and microorganisms, copolymers and/or derivatives and/or mixtures and/or chemical modifications of said polymers and any combination thereof, with different material parameters such as chain length or molecular weight.

The polymers may be utilized, for example, as excipients (e.g., for the incorporation and processing of active ingredients), as basic formulation substances (e.g., for cosmetics) or as separate active ingredients.

Representative active ingredients or classes of drugs that may be used or incorporated in accordance with the present invention include, but are not limited to, one or more immunoglobulins, fragments or fractions of an immunoglobulin, synthetic substances that mimic immunoglobulins, or such synthetic, semisynthetic or biosynthetic fragments or fractions, chimeric, humanized or human monoclonal antibodies, Fab fragments, fusion proteins or receptor antagonists (for example: anti-TNF-alpha, interleukin-1, interleukin-6 etc.), anti-angiogenic active substances (for example: anti-TNF-alpha; VEGF, anti-PDGF, etc.), inhibitors of intracellular signals (for example: JAK1, 3 inhibitors and SYK inhibitors), peptides with a molecular weight of greater than or equal to 3 kDa, ribonucleic acids (RNA), desoxyribonucleic acids (DNA), plasmids, peptide nucleic acids (PNS), steroids, corticosteroids, adrenocorticostatics, antibiotics, antidepressants, antifungals, sympatholytics, androgens or antiandrogens, antianemics, anabolic steroids, anesthetics, analeptics, antiallergic drugs, antiarrhythmics, antiatherosclerotic active substances, antifibrinolytics, anticonvulsants, anti-inflammatory substances, anticholinergics, antihistamines, antihypertensive substances, antihypotensive substances, anticoagulants, antiseptics, antihaemorrhagic substances, antimysthenic agents, antiphlogistics, antimalarials, antipyretics, beta-receptor antagonists, calcium channel blockers, cells, cell differentiation factors, chemokines, chemotherapeutics, coenzymes, cytotoxic agents, cytostatics, enzymes and their synthetic and biosynthetic analogues, glucocorticoids, growth factors, hemostats, hormones, their synthetic and biosynthetic analogs, immunosuppressants, immunostimulants, mitogens, physiological or pharmacological inhibitors of mitogens, mineralcorticoids, muscle relaxants, narcotics, neurotransmitters, precursors of neurotransmitters, oligonucleotides, peptides, (para-) sympathomimetics, (para) sympatholytics, proteins, sedative agents, spasmolytics, vasoconstrictors, vasodilators, vaccines, vectors, viruses, virus-like particles, antivirals, wound healing accelerators and combinations of these substances.

Representative solvent systems, solvent mixtures, multiphase solvent systems or mixtures are described herein. These include but are not limited to one or more liquid, inorganic or organic substances or mixtures thereof with different functional groups and therefore different solvent properties (rheological, physicochemical, chemical, etc.).

The present invention contemplates the use of one or more (bio-) polymer substances in conjunction with solvent mixtures or multiphase solvent systems having different affinities or dissolution properties with respect to the polymer substances. Of significance is the use of a solvent which is a good substrate/good solvent for the polymers used in conjunction with a solvent having poor solvent properties for the substance used. The dry powder of the polymer substance (which may be lyophilized) is blended with the solvent system, resulting in swelling or dissolution of the polymer. The solvent contained in the system with poor solvent properties with respect to the starting material prevents complete dissolution and causes phase separations and positive rheological properties of the total mixture. This total mixture can then be mixed or homogenized by mechanical methods (including but not limited to stirring systems, extruders, rotary-cut processes, 3-D printing processes, etc.) with little effort. Subsequent methods allow various uses of the masterbatch for product manufacturing.

The processes of the present invention produce highly reproducible results and have several advantages over previously used processing methods of polymers. The use of solvents with poor affinity for the polymer enables the preparation of highly concentrated multiphase systems with suitable and easily controllable (by proportions of solvent mixtures/systems) rheological properties. They prevent the formation of gels, or high-viscosity polymer structures at lower polymer concentrations, which hinder the further mechanical processing and adversely affect the drying behavior. Furthermore, the physicochemical properties of the solvents can be exploited to achieve further advantages in the fabrication. Thus, solvents such as ethanol or isopropanol can be used to minimize the number of colony forming units occurring in the polymer matrix (disinfecting effect) even at concentrations below 60% since the residual solvent with higher affinity for the polymer substance is absorbed and ethanol concentration rises. Furthermore, the use of such solvents allows extremely accelerated drying behavior due to the increased vapor pressure and the ability to remove and reuse excess low affinity solvent to the polymer matrix by means of compression molding.

The methods of the invention can also be carried out under pharmaceutically acceptable conditions and can lead to sterile products or to products of suitable quality and purity.

Furthermore, the present invention also contemplates uses of the formulations, which are obtained in accordance with the present invention, for the cosmetic and pharmaceutical markets (including but not limited to care products, medical products, and galenic preparations for the application of active ingredients to animals and humans).

A preferred polymer material, in accordance with the present invention, is hyaluronic acid with different molecular weights due to its special position in nature and the favorable profile of properties (high biocompatibility, high biodegradability, bacteriostatic properties, stabilization of biological agents, positive effects on blood coagulation and wound healing and general improvement of the skin appearance through water absorption and nourishing properties). However, it is not to be regarded as the main starting substance and can be replaced by other polymers/biopolymers and mixtures or derivatives thereof.

Furthermore, one or more active substances can be added to the base mixture in various ways in order to produce a suitable active ingredient-containing polymer matrix. For example, active ingredients can be dissolved or dispersed in the solvent mixture or multiphase solvent system and thus be distributed homogeneously into the matrix or added in the solid state to the dry polymer powder and distributed by suitable mechanical homogenization. Thus, a large variety of galenic formulations in the semi-solid (suspensions, emulsions, multiphase solvent systems) and (after drying and molding processes) in the dry state (including solid in all forms such as suppositories, tablets, screws or microneedles) can be fabricated.

According to preferred embodiments of the present invention, the mechanical processing methods after the preparation of the basic mixture are dependent on the previously processed materials and their properties and are product-oriented.

Drying can be carried out at various temperatures and under normal or elevated mechanical or atmospheric pressure, and, for example, in suitably shaped moulds such as stainless steel cavities or silicone cavities.

According to preferred embodiments of the present invention, solids obtained with the methods of the present invention, with or without active ingredients, can then be brought into a desired appearance, shape, size and structure by application of further mechanical processing methods (including, but not limited to, milling, cutting, turning, rotary-cut methods for microparticles, etc.).

Examples of Processing Methods

While certain embodiments utilize at least one active pharmaceutical ingredient in dry particulate form, it is also to be understood that the present invention also contemplates that the methods, processes and formulations of the present invention may, in other embodiments, also utilize one or more active pharmaceutical ingredients that are present in any other type of physical state, as well as active pharmaceutical ingredients dissolved in any suitable and appropriate solvent system as needed or desired.

Representative Processing Example A:

The following substances are given in a suitable vessel and are processed accordingly:
Polymer in dry particulate form
(optional: excipients in dry particulate form)
(optional: active ingredients in dry particulate form)
A single-phase multicomponent system of solvents
Homogenization of the mixture by mechanical means
(optional: removal of excess solvent with poor solvent properties with respect to polymer mass)

Representative Processing Example B:

The following substances are given in a suitable vessel and are processed accordingly:
Polymer in dry particulate form
(optional: excipients in dry particulate form)
(optional: active ingredients in dry particulate form)
A multiphase system of solvents (solvents not miscible)
Homogenization of the given ingredients by mechanical energy input until homogeneous mixture is obtained
(Optional: removal of excess solvent with poor solvent properties with respect to polymer mass by pressure, increased air circulation, etc.)

Representative Processing Example C:

The following substances are given in a suitable vessel and are processed accordingly:
Polymer in dry particulate form
A single-phase multicomponent system of solvents with dissolved active substances or excipients
Mixing of the given ingredients by mechanical energy input until homogeneous mixture is obtained (Optional: removal of excess solvent with poor solvent properties with respect to polymer mass by pressure, increased air circulation, etc.)

Representative Production Example D:

The following substances are given in a suitable vessel and are processed accordingly:

Polymer in dry particulate form

A multi-phase system of solvents with dissolved active substances or excipients

Mixing of the given ingredients by mechanical energy input until homogeneous mixture is obtained (Optional: removal of excess solvent with poor solvent properties with respect to polymer mass by pressure, increased air circulation, etc.)

Representative Production Example E:

The following substances are given in a suitable vessel and are processed accordingly:

Polymer in dry particulate form (optional: excipients in dry particulate form)

(optional: active ingredients in dry particulate form)

A solvent with poor solvent properties with respect to the polymer/substance mixture Mixing of the given ingredients by mechanical energy input until homogeneous mixture is obtained (preparation of a suspension intended for storage)

Addition of a solvent that dissolves or swells the contained solids to activate the system prior to direct use Representative Examples of Further Processing of Examples A-D:

3-D printing: With the aid of different solvent mixtures, special rheological properties of the basic mixtures can be set, which can then be brought into desired shapes by means of computer-controlled 3-D printing (via, for example, extrusion nozzles) and solidified by drying.

Molding in cavities: The basic mixtures mentioned in Examples A-E can be pressed under short-term or permanent pressure in cavities or molds made of different materials (e.g. silicone, stainless steel, solid resins, inorganic materials, etc.) and dried/solidified before or after removal from the mould. Any residues of solvents can be removed by these means.

Further Processing by Reagents/Reaction Conditions: The basic mixtures mentioned in Examples A-E can be mixed with other reagents after their preparation or can be exposed to specific reaction conditions in order to covalently or ionically combine/bind the polymer molecules. This could slow down later dissolution processes or add/supplement further physicochemical properties of the material.

Mechanical Processing: The basic mixtures mentioned in Examples A-E can be mechanically further processed after their drying and solidification by means of milling, cutting or lancing processes to be able to produce solids of any desired shape. Furthermore, solidified bodies can be brought into particulate forms by means of suitable grinding methods with a defined particle size and particle surface.

Representative Examples of the Use of the Basic Mixtures Mentioned in Examples A-E With and Without Further Processing:

Microneedles: By pressing into a negative/female mold microneedles/arrays of microneedles of all conceivable shapes and geometries, number of needles and patch sizes, polymer microneedles can be made for topical transdermal or intradermal application.

In this case, purely cosmetic formulations are conceivable (without active ingredients) and formulations for use in the pharmaceutical market (with one or more of the active ingredients described herein). The microneedles can be used, for example, for topical application (for example, but not limited to itchy, irritated or inflamed skin areas, insect bites, infections or diseases, etc.) or for drug release throughout the body (for example, but not exclusively for vaccine application, application of biological highly potent active pharmaceutical ingredients (API's) of BCS Class 3, etc.). Microneedles of this type may also be provided with an adhesive layer or possess a natural adhesive layer to be attached to the skin area for a longer time or stay only short-term in place at the body.

Films of different thicknesses: The base materials can be processed to films of different thicknesses by applying them to a bandage or plaster base with usage of pressure. Such films may find application as a wound dressing (for example, but not limited to, wetting wounds, burns or dry skin areas and others) or as a drug-containing patch for the transdermal delivery of drugs. Further application of these films include incorporation into body cavities for moistening or stimulating wound healing processes.

Solid bodies: By further processing with the methods already mentioned herein polymer solids of various sizes and shapes can be produced. These can find various applications including: clamps, screws, scaffolds, solid dosage forms, combs, ornaments, vascular occlusions, nails, buttons and many more. Depending on the polymer used, introduction/implantation into the human body is conceivable for mechanical stabilization or for the administration of one or more active substances.

Stable suspensions of biopolymers: As mentioned in Example E, stable suspensions of polymers can be prepared by means of the polymer particles previously defined in terms of particle size and particle surface. Such suspensions can, for example, consist exclusively of nourishing oil and defined hyaluronic acid particles for exfoliation/peeling of skin areas. Subsequently, a quasi-emulsion can be formed by water application, which causes further moisturizing and nourishing properties for the skin. In addition, active substances can be incorporated in oil or particles for transdermal application.

Examples for the Preparation of the Matrix and Solid Bodies

Preparation of a Basic Mixture With Na-Hyaluronate (High Molecular Weight):

5.067 g of Na-hyaluronate (high molecular weight of 1.5 MDa) is mixed with 8.3 ml of 70% aqueous isopropanol solution by homogenization through usage of IKA Tube Mill at 25,000 rpm for 15 seconds. After 5 minutes a homogeneous swelling of the polymer matrix with the water contained in the solution is achieved.

The thus obtained basic mixture is pressed into a silicone cavity while the excess amount of isopropanol is emerging from the mass during drying/under pressure.

Furthermore, the pressed polymer bodies are dried at 60° C. for 24 hours in a drying oven.

Preparation of the Basic Mixture With Na-Hyaluronate (Low Molecular Weight)

5.007 g of Na-hyaluronate (low molecular weight of 4500 Da) is mixed in a bowl with 8.3 ml of 70% aqueous isopropanol solution by stirring. After a swelling time of 5 minutes, the matrix is shaped by pressure into a silicone mold (with removal of the excess isopropanol) and dried at 60° C.

The invention claimed is:

1. A method of processing a biopolymer, comprising:
providing the biopolymer in dry particulate form, wherein the biopolymer is hyaluronic acid or a hyaluronate salt;
optionally providing at least one active pharmaceutical ingredient;

providing a single-phase solvent solution consisting of 30%-40% water and 60%-70% isopropanol or ethanol;

combining the biopolymer in dry particulate form with the single-phase solvent solution, and optionally the at least one active pharmaceutical ingredient; and mixing the combined mixture by mechanical means to produce a biopolymer matrix having a homogenous swelling.

2. The method of claim 1, further comprising removing excess isopropanol or ethanol from the produced biopolymer matrix by pressure and/or air circulation.

3. The method of claim 1, further comprising forming a pressed body from the biopolymer matrix.

4. The method of claim 3, wherein the pressed body is microneedles or a film.

5. The method of claim 1, further comprising pressing the biopolymer matrix in a cavity or mold, and drying and/or solidifying before or after removal from the cavity or mold.

6. The method of claim 5, wherein the cavity or mold is shaped for microneedles.

7. The method of claim 1, further comprising forming a film from the biopolymer matrix.

8. The method of claim 7, further comprising applying the film to a bandage or plaster base.

9. The method of claim 1, wherein the biopolymer in dry particulate form and the single-phase solvent solution are combined in an amount of about 0.60-0.61 g biopolymer to about 1 ml solvent solution.

10. The method of claim 1, wherein the at least one active pharmaceutical ingredient is provided.

11. The method of claim 1, wherein the method is carried out under sterile conditions to produce a sterile biopolymer matrix.

* * * * *